United States Patent [19]

Gunasekera et al.

[11] Patent Number: 4,866,084
[45] Date of Patent: Sep. 12, 1989

[54] TOPSENTIN COMPOUNDS EFFECTIVE AGAINST VIRUSES AND CERTAIN TUMORS

[75] Inventors: Sarath P. Gunasekera, Vero Beach; Sue S. Cross, Ft. Pierce, both of Fla.; Yoel Kashman, Tel Aviv, Israel; May S. Lui, Sebastian, Fla.; Kenneth L. Rinehart, Urbana, Ill.; Shinji Tsujii, Okayama, Japan

[73] Assignee: Harbor Branch Oceanographic Institution, Inc., Ft. Pierce, Fla.

[21] Appl. No.: 286,221

[22] Filed: Dec. 19, 1988

Related U.S. Application Data

[63] Continuation-in-part of Ser. No. 277,516, Sep. 28, 1988, abandoned, which is a continuation of Ser. No. 168,598, Mar. 4, 1988, abandoned, which is a continuation of Ser. No. 935,401, Nov. 26, 1986, abandoned, and a continuation-in-part of Ser. No. 74,978, Jul. 17, 1987, abandoned.

[51] Int. Cl.⁴ .................. A61K 31/415; C07D 403/14
[52] U.S. Cl. ..................................... 514/397; 514/402; 548/336; 548/348
[58] Field of Search ................ 548/348, 336; 514/402, 514/397

[56] References Cited

U.S. PATENT DOCUMENTS 4,217,357 8/1980 Cross et al. .................... 548/336 X Primary Examiner—Richard A. Schwartz
Attorney, Agent, or Firm—Carroll F. Palmer

[57] ABSTRACT

A new class of novel, biologically active bisindole alkaloid compounds, which have been named topsentins, pharmaceutical compositions containing them, methods of producing the compounds and methods of using them are disclosed. This new class of compounds has the generic formula:

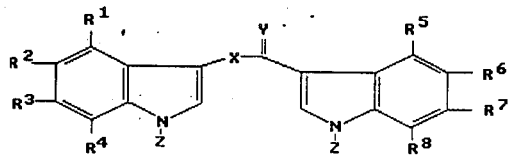

Wherein X =

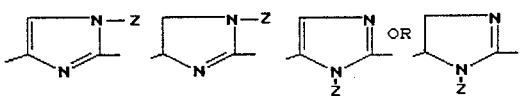

$R^{1-8}$ are the same or different selected from —H, —OH, halogen, —R, —OR, —OCOR, or —OA;

Y is the single group —O, or two groups, same or different, selected from —H, —OH, —OR, or —OCOR with the provision that Y shall not be two —OH groups;

Z are the same or different selected from —H, —R;

R is C1-5 alkyl and A is —R—phenyl.

The compounds are antiviral agents and antitumor agents which are effective against specific tumors.

8 Claims, No Drawings

TOPSENTIN COMPOUNDS EFFECTIVE AGAINST VIRUSES AND CERTAIN TUMORS

CROSS-REFERENCE TO RELATED APPLICATION

This application is a continuation-in-part of application Ser. No. 277,516, filed Sept. 28, 1988, now abandoned, which is a continuation of application Ser. No. 168,598, filed Mar. 4, 1988, which in turn, is a continuation of Ser. No. 935,401, filed Nov. 26, 1986, now abandoned, and a continuation-in-part of copending application Ser. No. 074,978, filed July 17, 1987, now abandoned.

FIELD OF THE INVENTION

This application relates to novel bis-indole alkaloid compounds and compositions containing such compounds as active ingredients. More particularly, the invention concerns a new class of biologically active compounds which have been named topsentins, pharmaceutical compositions containing them methods of producing the compounds and methods of using them.

BACKGROUND OF THE INVENTION

Considerable research and resources have been devoted to oncology and antitumor measures including chemotherapy. While certain methods and chemical compositions have been developed which aid in inhibiting, remitting or controlling the growth of tumors, new methods and antitumor chemical compositions are needed.

The prevention and control of viral diseases is also of prime importance to man and much research has been devoted to development of antiviral measures. Certain methods and chemical compositions have been developed which aid in inhibiting, controlling or destroying viruses, but additional methods and antiviral compositions are needed.

It has been found that some natural products and organisms are potential sources for chemical molecules having useful biological activity of great diversity. Marine sponges have proved to be such a source and a number of publications have issued disclosing organic compounds derived from marine sponges including Scheuer, P. J. Ed., Marine Natural Products, Chemical and Biological Perspectives; Academic Press, New York, 1978-1983, Vol. I-V; Faulkner, D. J., Natural Products Reports 1984, 1, 551-598; 1986, 3, 1-33 & 1987, 4, 539-576; J. Am. Chem. Soc., 1985, 107, 4796-4798.

Indole compounds of marine origin have also been described in Tetrahedron Letters, 1984, 25, 5047-5048 and J. Am. Chem. Soc., 1982, 104, 3628-3635.

This present invention, utilizing sponges as a source material and supplemented by novel synthetic production methods, has provided the art with a new class of biologically active compounds and new pharmaceutical compositions useful as antitumor agents effective against specific tumors and antiviral agents.

Other advantages and further scope of applicability of the present invention will become apparent from the detailed descriptions given herein; it should be understood, however, that the detailed descriptions, while indicating preferred embodiments of the invention, are given by way of illustration only, since various changes and modifications within the spirit and scope of the invention will become apparent from such descriptions.

SUMMARY OF THE INVENTION

The objects of the invention are accomplished by the provision of a novel class of biologically active compounds that have been named topsentins and have a structure according to the formula:

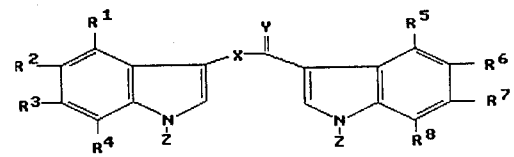

Wherein X =

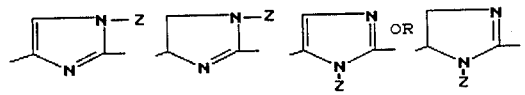

$R^{1-8}$ are the same or different selected from —H, —OH, halogen, —R, —OR, —OCOR, or —OA;

Y is the single group $\neq$O, or two groups, same or different, selected from —H, —OH, —OR, or —OCOR with the provision that Y shall not be two —OH groups;

Z are the same or different selected from —H, or —R;

R is C1-5 alkyl and A is -R-phenyl.

A preferred group of compounds of the invention are those of the formula:

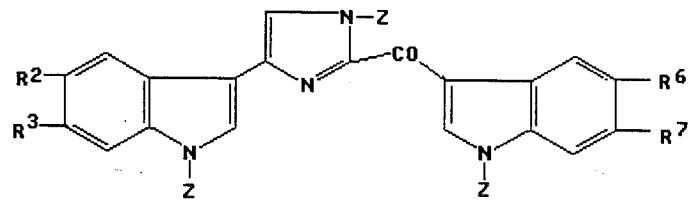

wherein $R^2$ & $R^6$ are —H while $R^3$ & $R^7$ are —H, —OH, halogen, —R, —OR, —OCOR or —OA; or $R^3$ & $R^7$ are —H while $R^2$ & $R^6$ are —H, —OH, halogen, —R, —OR, —OCOR or —OA; Z are the same or different selected from —H, —R; R is C1-5 alkyl and A is -R-phenyl.

Particularly preferred compounds of the invention are those of the formula:

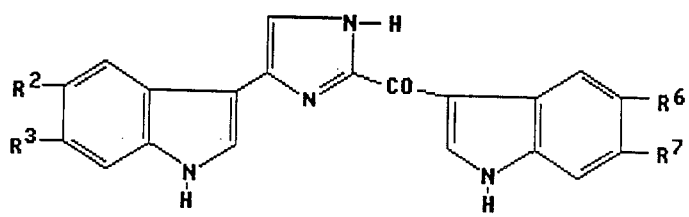

wherein:
1: $R^2$, $R^3$, $R^6$=H; $R^7$=OH (Topsentin)
2: $R^2$, $R^6$=H; $R^3$=Br; $R^7$=OH (Bromotopsentin)
4: $R^2$, $R^6$, $R^7$=H; $R^3$=OH (Isotopsentin)
5: $R^2$, $R^6$=H; $R^3$, $R^7$=OH (Hydroxytopsentin)
6: $R^2$, $R^3$, $R^6$, $R^7$=H (Deoxytopsentin)
7: $R^2$, $R^3$, $R^7$=H; $R^6$=OH (Neotopsentin)
8: $R^3$, $R^6$, $R^7$=H; $R^2$=OH (Neoisotopsentin)
9: $R^2$, $R^6$=OH; $R^3$, $R^7$=H (Neohydroxytopsentin)

As a result of the discoveries by the invention of the new compounds as delineated above, skilled chemists will be able to use procedures as disclosed herein and others to synthesize these compounds from available stock substances. In carrying out such operations, any suitable filtration, chromatographic and other purification techniques may be utilized. Suitable chromatography techniques include reversed phase, medium pressure and high pressure liquid chromatography (RPLC, MPLC AND HPLC, respectively) with a suitable column as would be known to those skilled in the art including silica gel, Sephadex LH-20, ammonia-treated silica gel and LiChrosorb $NH_2$ columns. Such columns are eluted with suitable eluents such as heptane, ethyl acetate, methylene chloride, methanol, isopropyl alcohol and various combinations and ratios thereof.

As embodied and fully described herein, the invention also comprises pharmaceutical compositions, e.g., antiviral and antitumor compositions, which antitumor compositions are effective against specific tumors, containing as active ingredient an effective amount, preferably between about 0.1 to 45%, especially 1 to 25%, by weight based on the total weight of the composition, of one or more compounds according to the formulae expressed above and a non-toxic, pharmaceutically acceptable carrier or diluent.

As embodied and fully described herein, the invention also comprises processes for the production of the new compounds and compositions of the invention and methods of use thereof, e.g., methods of inhibiting certain tumors in a mammal, therapeutic methods for treating cancerous cachexia and methods of inhibiting viruses.

In accordance with the invention, methods for inhibiting certain tumors in a host comprise contacting tumor cells with an effective amount of the new pharmaceutical compositions of the invention and methods for inhibiting viruses comprise administering to the host an effective amount of the new pharmaceutical compositions of the invention.

DESCRIPTION OF THE PREFERRED EMBODIMENTS

A more complete understanding of the invention can be obtained by reference to preferred embodiments of the invention which are illustrated by the following specific examples of compounds, compositions and methods of the invention. It will be apparent to those skilled in the art that the examples involve use of materials and reagents that are commercially available from known sources, e.g., chemical supply houses, so no details are given respecting them.

One method of preparation of the new compounds of the invention involves extraction from marine sponges of the Order Halichondrida (Phylum Porifera, Class Demospongiae) which is a problematic taxonomic group, with generic distinctions not clearly defined. Four samples used in connection with this invention have been assigned to the genus Spongosorites, Topsent 1896, a genus characterized by: a distinct and thick (up to 1 mm) dermal layer of smaller spicules arranged tangentially to the surface; a confused choanosomal arrangement of spicules with sporadic vague spicule tracts running parallel to the surface; bright-yellow color when alive, turning brown or black when preserved in alcohol; and two or three size categories of straight or crooked oxea. Spongosorites sp.1 (4-XII-84-1-22, black in alcohol) has crooked oxea and is distinguished by association with vermetids (Phylum Mollusca, Class Gastropoda); Spongosorites sp.3 (4-XII-84-1-23 and 23-VIII-85-1-39, tan-brown in alcohol) has fusiform straight oxea. Voucher samples are deposited on the Indian River Coastal Zone Museum of Harbor Branch Oceanographic Institution at Ft. Pierce, Fla., and species names will be assigned when revision of the Order Halichondrida has been completed by Dr. R. Van Soest, Institute for Taxonomic Zoology, University of Amsterdam, with Dr. Shirley A. Pomponi and M. Cristina Diaz.

EXAMPLE 1

This example concerns the preparation of topsentin 1 and bromotopsentin 2.

The frozen sample (264 g) of marine sponge, *Spongosorites ruetzleri*, (Van Soest and Stentoft 1988), collected at a depth of 1149 feet at Goulding's Cay, Bahamas, was extracted twice with methanol-toluene (3:1). The combined extracts on concentration on a water bath at 30 C. in vacuo gave as a residue (11.32 g) of crude extract which was partitioned between pentane and 10% aqueous methanol. The alcohol layer was then diluted to 30% water and extracted with $CH_2Cl_2$. The aqueous methanol layer was concentrated and partitioned between butanol and water. A portion (200 mg) of the *Herpes simplex* virus type 1 (HSV-1)-active, butanol-soluble fraction was dissolved in 20% aqueous methanol (1 ml) and chromatographed on a column (ID=22 mm, height=40 mm) packed with reversed-phase material (Amicon silica—C8, 20–45 μm). The active fraction (123 mg) was eluted with 20% aqueous methanol and purified by reversed-phase HPLC (IBM 5μ, C18, 10 mm×250 mm, 20% aqueous methanol) to yield pure topsentin 1, 20 mg. and bromotopsentin 2, 67 mg as yellow powder.

Topsentin, amorphous, bright-yellow solid, mp>250° C. when analyzed by conventional methods and apparatus, produced the following spectral data:

UV absorption, λmax (MeOH) 208 nm (ε12,000), 246 sh (5100), 285 (4500) and 375 (4600);

IR (KBr) 3395, 3275, 1635, 1590, 1530, 1455, 1270, 1165, 1115, 1095, 1005 and 876 cm$^{-1}$;

$^1$H NMR (360 MHz, DMSO-d$_6$+1% TFA-H) 6.841 (1H, dd, J=8.6, 1.8 Hz), 6.997 (1H, d, J=1.8 Hz), 7.201 (2H, m), 7.523 (1H, d, J=7.9 Hz), 7.990 (1H, d, J=7.6 Hz), 8.041 (1H, d, J=8.6 Hz), 8.155 (1H, d, J=2.8 Hz), 8.159 (1H, s), 8.487 (1H, d, J=3.2 Hz), 11.762 (1H, s), 12.355 (1H, d, J=2.2 Hz);

$^{13}$C NMR (90 MHz, DMSO+1%TFA-H) 98.11(d), 102.72(s), 113.12(d), 113.95(s), 116.00(d), 118.67(s), 119.46(d), 120.50(d), 122.02(d), 122.44(d), 124.27(s), 125.74(d), 131.11(s), 136.53(s), 137.78(d), 138.33(s), 141.23(s), 155.25(s), 171.5(s);

EIMS 342 (100%, C$_{20}$H$_{14}$N$_4$O$_2$, M+), 209 (39, C$_{12}$H$_7$N$_2$O), 183 (28, C$_{11}$H$_9$N$_3$), 171 (17, C$_{10}$H$_7$N$_2$O), 160 (145, C$_9$H$_6$NO$_2$), 133 (65, C$_8$H$_7$NO) and 105 (15).

Bromotopsentin, yellow crystals, m.p. 296°-7° C. when analyzed by conventional methods and apparatus, produced the following spectral data:

UV absorption, λmax (MeOH) 209 nm (ε13,000), 236 (9700), 287 (5000) and 374 (5800);

IR (KBr) 3400-3100, 2255, 2120, 1635, 1590, 1520, 1445, 1265, 1230, 1165, 1028, 1005 and 875 cm$^{-1}$;

$^1$H NMR (360 MHz, CDCl$_3$:CF$_3$COOH:1:1) 7.098 (1H, dd, J=8.6, 2.4 Hz), 7.193 (1H, d, J=2.4 Hz), 7.227 (1H, dd, J=8.6, 1.8 Hz), 7.558 (1H, d, J=8.6 Hz), 7.668 (1H, d, J=1.8 Hz), 7.824 (1, s), 7.927 (1H, d, J=3 Hz), 8.202 (1H, d, J=8.6 Hz), 8.371 (1H, d, J=3 Hz), 9.272 (1h, brs), 10.409 (1H, brs);

$^{13}$C NMR (90 MHz, CDCl$_3$:CF$_3$COOH 1:1) 101.6(d), 103.7(s), 116.7(d), 117.0(s), 117.6(d), 118.2(d), 119.6(s), 121.5(d), 122.6(s), 125.2(s), 125.5(d), 127.7(d), 128.0(d), 135.0(s), 139.7(s), 140.5(s), 140.8(d), 141.7(s), 155.0(s), 172.4(s);

EIMS 422/420 (40%, C$_{20}$H$_{13}$BrN$_4$O$_2$, M+), 394/392 (1.3, C$_{19}$H$_{11}$BrN$_3$O$_2$), 342 (13, M+-Br), 289/287 (6%, C$_{12}$H$_7$BrN$_3$O), 263/261 (100, C$_{11}$H$_8$BrN$_3$), 223/221 (13, C$_9$H$_6$BrN$_2$), 209/207 (9.5, C$_9$H$_6$BrNO), 182 (15, 261-Br) and 133 (94, C$_8$H$_7$NO).

EXAMPLE 2

This example concerns the conversion of bromotopsentin to topsentin.

Bromotopsentin in absolute ethanol was stirred vigorously with 10% palladium on activated carbon under hydrogen at room temperature for 4 hrs. The reaction mixture was filtered and washings were evaporated in vacuo to give a quantitative yield of topsentin identical to natural topsentin in LREIMS and $^1$H NMR spectra.

EXAMPLE 3

Frozen sponge sample of Spongosorites sp.3 collected at Goulding's Cay, Bahamas at −229 m was homogenized and steeped repeatedly in methanol and 10% toluene followed by methanol. The alcohol layer was concentrated and re-partitioned between 1-butanol and water, and the butanol-soluble fraction was vacuum chromatographed over RP material (Amicon, silica gel C18, 20–45 μm) using 20% aqueous methanol. The yellow fraction was then subjected twice to RP-HPLC (C18, 5 μm, 20% water in MeOH) to give bromotopsentin 2 and 4,5-dihydro-6''-deoxybromotopsentin 3 of the formula:

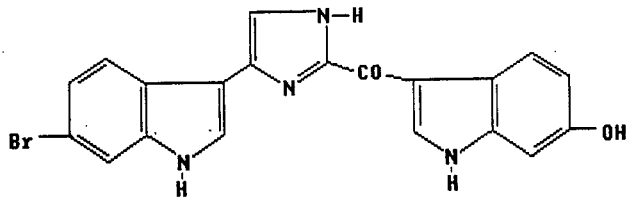

Compound 3 is a yellow powder with the following spectral data:

[α]$^{24}$D 198° (c 2.0, MeOH).

UV (MeOH) λmax nm 328 (ε5700), 274 (8800), 214 (34,000), 198 (29,500);

IR (KBr) 3620, 3390, 3280, 2920, 2860, 1665, 1570, 1450, 1420, 1332, 1240, 1160, 1120, 1100, 1020, 950, 805 and 750 cm$^{-1}$;

LREIMS m/z (rel intensity) 406(95), 404(100), 378(41), 376(39), 326(10), 298(6), 297(7), 291(10), 289(9), 235(6), 233(6), 210(12), 208(10), 197(10), 195(10), 189(5), 156(12), 155(19), 144(28), 130(14).

$^1$H and $^{13}$C NMR collected data also supported the structure given above.

Calcd for C$_{20}$H$_{13}$$^{79}$BrN$_4$O: 404.0272 (M-2H). Found 404.0300 (HREIMS).

EXAMPLE 4

This example concerns the preparation of 3-(hydroxyacetyl)indole 12 as a synthon.

3-(Chloroacetyl)indole was prepared in 34% yield according to a known procedure (Bergman, J. Heterocycl. Chem. 1970, 7, 1071–1076) and characterized by spectral data. The product was added to formamide-water (10:1) and stirred at 110 C. for 3.5 hrs. The reaction mixture was treated with a large excess of 14% aqueous ammonia and extracted with chloroform. After evaporation, the crude product (65 mg) was purified by RP(MP)LC (Waters C18; MeOH:H$_2$O:3:1) to give 12 in 97% yield as colorless needles, mp 173-174 C.

Calcd for C$_{10}$H$_9$NO$_2$: 175.0633. Found: 175.0633 (HREIMS).

EXAMPLE 5

This example concerns the preparation of 3-chloroacetyl-6-(benzyloxy)indole 11 as a synthon.

6-(Benzyloxy)indole dissolved in a mixture of dioxane and pyridine was stirred at 60 C. under nitrogen while chloroacetyl chloride in dioxane was added dropwise during 1 hr. The reaction mixture was then stirred for another 0.5 hr. and poured into diethyl ether-water. The precipitate was collected by filtration and washed thoroughly with cold diethyl ether to yield 47% of 11 as an orange solid.

Calcd for C$_{17}$H$_{14}$$^{35}$ClNO$_2$: 299.0713 Found: 299.0713 (HREIMS).

EXAMPLE 6

This example concerns the preparation of 3-hydroxyacetyl-6-(benzyloxy)indole 13 as a synthon.

A solution of 11 in dioxane was added to formamide-water (10:1). The mixture was stirred at 110° C. for 10 hrs., then worked up and purified as described above to yield 82% of 13 as colorless prisms with mp 194°–195° C. (EtOAc).

Calcd for $C_{17}H_{15}NO_3$: 281.1052. Found: 281.1047 (HREIMS).

EXAMPLE 7

This example concerns the synthesis directly from (hydroxylacetyl)indoles of O-benzyltopsentin 16, O-benzylisotopsentin 17, O,O'-dibenzylhydroxytopsentin 18, and deoxytopsentin 6.

Copper(II) acetate monohydrate (506 mg) in 30% aqueous ammonia (10 ml) was added dropwise to a refluxing, stirred mixture of 3-(hydroxyacetyl)indole 12 (136 mg) and 3-hydroxyacetyl-6-(benzyloxy)indole 13 in ethanol (20 ml) during 5 min. After addition was completed, the reaction mixture refluxed for another 10 min., then was allowed to cool to room temperature. Hydrogen sulfide gas was bubbled through the solution for 5 min. Filtration and evaporation gave a brown solid. Column chromatography ($SiO_2$, 20 g; $CHCl_3$:MeOH:50:1) followed by RP-MPLC (Waters C18, 50 g; MeOH:$H_2O$:3:1–4:1) and HPLC (Alltech C18, MeOH:$H_2O$:7:3) gave 16, 17, 18 and 6 with recovered 12 and 13.

EXAMPLE 8

This example concerns the preparation of 6 & 16–18 from isolated glyoxalkyl intermediates.

Copper(II) acetate monohydrate in 50% aqueous acetic acid was added to 12 in ethanol. The mixture refluxed with stirring for 4 hrs., then was allowed to cool to room temperature, filtered through "Celite" and evaporated at reduced pressure. Water was added and the aqueous layer was extracted with ethyl acetate. The combined organic phase was washed with water, saturated with aqueous $NaHCO_3$ and brine. It was then evaporated in vacuo to give nearly pure 3-glyoxalylindole 14.

Similarly, 13 in ethanol was treated with copper(II) acetate monohydrate in 50% aqueous acetic acid. Work-up gave nearly pure 3-glyoxalkyl-6-(benzyloxy)indole 15.

14 and 15, both prepared as above, were dissolved in 75% aqueous EtOH. Ammonia gas was bubbled through the solution for 15 min. at room temperature, then for another 15 min. under reflux. After cooling, the solvent was removed in vacuo, and the residue was purified by column chromatography ($SiO_2$, $CHCl_3$:MeOH:50:1) followed by RP-MPLC (Waters C18, MeOH:$H_2O$ 1:1–3:1) and HPLC (Merck LiChrosorb $NH_2$, 7 μm; $CHCl_3$:MeOH:10:1) to obtain 16, 17, 18 and 6.

O-Benzyltopsentin 16 is a bright yellow solid whose structure was established by spectral analysis.

Calcd for $C_{27}H_{20}N_4O_2$: 432.1586 Found: 432.1594 (HREIMS).

O-Benzylisotopsentin 17 is a bright yellow solid whose structure was established by spectral analysis. Calcd for $C_{27}H_{20}N_4O_2$: 432.1586 Found: 432.1594 (HREIMS). O,O'-Dibenzylhydroxytopsentin 18 is a bright yellow solid, mp>250° C., whose structure was established by spectral analysis. Calcd for $C_{34}H_{26}N_4O_3$: 538.2005 Found: 538.2003 (HREIMS).

Deoxytopsentin 6 is a bright yellow solid, mp>250 C., whose structure was established by spectral analysis.

EXAMPLE 9

This example concerns the conversion of O-benzyltopsentin to topsentin.

A solution of 16 in absolute EtOH was stirred vigorously with 10% palladium on activated carbon under hydrogen at room temperature for 10 hr. The reaction mixture was filtered through "Celite" and washed thoroughly with EtOH. After evaporation of EtOH, topsentin was obtained in quantitative yield. The synthesized topsentin was identical with natural topsentin in spectral data and in biological activities.

EXAMPLE 10

This example concerns the conversion of O-benzylisotopsentin 17 to isotopsentin 4.

A solution of 17 in absolute EtOH was treated with 10% palladium on activated carbon as for 16 in Example 9 to give 4 in quantitative yield, a yellow, amorphous solid whose structure was established by spectral data.

EXAMPLE 11

This example concerns the synthesis of hydroxytopsentin 5 from 3-hydroxyacetyl-6-(benzyloxy)-indole 13.

Ammonia gas was bubbled for 15 min. through a solution of 15, prepared as in Example 8 from 13, in 75% aqueous EtOH, then the mixture refluxed for another 15 min. The precipitate was collected by filtration and washed with methanol to yield 18. The combined filtrate and washings were purified by column chromatography to give an additional amount of 18 (total yield 63% from 13).

The precipitate of 18 was dissolved in methanol and the solution was stirred vigorously with 10% palladium on activated carbon under hydrogen at room temperature for 2 hrs. Work-up as described for the synthesis of 1 and 4, followed by RP-MPLC purification gave 5 (89%), a yellow solid whose structure was established by spectral data. Calcd for $C_{20}H_{14}N_4O_3$: 358.1066 Found: 358.1074 (HREIMS).

EXAMPLE 12

This example concerns the preparation of 3-chloroacetyl-5-(benzyloxy)indole 19.

5-(Benzyloxy)indole in dioxane containing pyridine was stirred for 1 hr. at 65° C. under nitrogen while chloroacetyl chloride in dioxane was added dropwise. The reaction mixture was stirred for another 1 hr., then poured into diethyl ether-water. The precipitate was collected by filtration and washed thoroughly with cold $Et_2O$ to yield 19, an orange solid.

Calcd for $C_{17}H_{14}{}^{35}ClNO_2$: 299.0713 Found: 299.0715 (HREIMS).

EXAMPLE 13

This example concerns the preparation of 3-hydroxyacetyl-5-(benzyloxy)indole 20.

A solution of 19 in dioxane was added to formamide-water (10:1) and the mixture was stirred at 110° C. for 6.5 hrs., then was worked up as for 12 above. Purification by column chromatography gave 20 (55%) whose structure was established by spectral data. Calcd for $C_{17}H_{15}NO_3$: 281.1052 Found: 281.1052 (HREIMS).

EXAMPLE 14

This example concerns the synthesis of neohydroxytopsentin 9.

A solution of 20 in ethanol was treated with copper-(II) acetate monohydrate in 50% aqueous acetic acid as described above for 15. Work-up gave nearly pure 3-glyoxalyl-5-(benzyloxy)indole 21.

Ammonia gas was bubbled for 15 min. through a solution of 21 in 75% aqueous EtOH and the mixture refluxed for another 15 min. After evaporation, the crude product was purified by column chromatography to give O,O'-dibenzylneohydroxytopsentin 24 (60%), a yellow amorphous solid whose structure was established by spectral data.

A solution of 24 in MeOH was stirred vigorously with 10% palladium on activated carbon under hydrogen at room temperature for 3 hrs. Work-up in the usual manner gave a crude product which was purified by HPLC to give 9, a bright-yellow, amorphous solid whose structure was established by spectral data.

Calcd for $C_{20}H_{14}N_4O_3$: 358.1031 Found: 358.1031 (HREIMS).

EXAMPLE 15

This example concerns the synthesis of neotopsentin 7 and neoisotopsentin 8.

Ammonia gas was bubbled through a solution of 14 (prepared from 12) and 21 (prepared from 20) in 75% aqueous EtOH, then for another 15 min. under reflux. After cooling, the solvent was removed in vacuo and the residue was purified by column chromatography followed by RP-MPLC, then by HPLC to obtain benzylneotopsentin (11%), benzylisotopsentin 23 (9%), dibenzylneohydroxytopsentin 24 (3%) and 6 (28%).

Compound 22 in MeOH was stirred vigorously with 10% palladium on activated carbon under hydrogen at room temperature for 3 hrs. The reaction mixture was filtered through "Celite" and washed thoroughly with EtOH. Evaporation of EtOH gave 7 (90%), a bright yellow, amorphous solid whose structure was established by spectral data. Found for $C_{20}H_{14}N_4O_2$: 342.1118 (HREIMS).

Compound 24 in MeOH was treated with 10% palladium on activated carbon under hydrogen at room temperature for 3 hrs and worked up as for 7 above to give 8 (86%), a bright yellow, amorphous solid whose structure was established by spectral data. Found for $C_{20}H_{14}N_4O_2$: 342.1114 (HREIMS).

ANTITUMOR ACTIVITIES OF THE NEW COMPOUNDS

The following assay method was utilized to illustrate the antitumor effectiveness of the compounds of the invention.

P388 IN VITRO ANTITUMOR SCREEN

Cell Culture. P388 murine leukemia cells, obtained from the National Cancer Institute, Bethesda, MD, were maintained at 37° C. in 5% $CO_2$ in humidified air. Growth medium was Roswell Park Memorial Institute medium 1640 supplemented with 10% heat-inactivated horse serum. Stock cultures of P388 cells were grown in antibiotic-free growth medium and were subcultured ($10^5$ cells/ml, 25 ml cultures in T-25 plastic tissue culture flasks) every 2-3 days. Every 3-4 months, stock cultures were reinitiated from frozen cells that were demonstrated to be free of mycoplasma contamination. To determine if organisms possess compounds having activity against P388 cells, extracts were diluted in methanol and added to cultures of P388 cells. An appropriate volume of the dilution was transferred to duplicate wells in a 96-well plate, evaporated to dryness, and 200 µl of growth medium containing cells at a density of $1 \times 10^5$ cells/ml was added per well. (Final concentration of extract was 20 µg/ml.) Each plate included six wells containing untreated cells for control growth (mean generation time was 15.2±0.7 hr, n=26 separate determinations) and replicate wells containing fluorouracil (0.2 µg/ml, ca. 95% inhibition of cell replication) as a positive control. For daily quality control, each technician determines the $IC_{50}$ of fluorouracil for inhibition of P388 cell proliferation. After 48-hour incubations, cell number was determined with the MTT assay (below), calculated as a percent of untreated cell growth, converted to percent inhibition, and reported to the chemist requesting the screen.

Determination of $IC_{50}$ Values. The initial determination of an $IC_{50}$ value for inhibition of P388 cell proliferation with a crude, semipure, or pure sample was made by diluting the sample in methanol to the appropriate concentration and then serial 1:1 dilutions were made in duplicate in a 96-well plate, such that the final concentrations in the assay were 20, 10, 5, 1.25, and 0.625 µg/ml. After solvent was evaporated to dryness, cells were added to each well as described above. After 48-hour incubations, cell numbers were determined with the MTT assay, converted to percent control, plotted versus the log of the sample concentration. Curves were fitted by least-squares linear regression of logit-transformed data and the concentration of sample that inhibited cell proliferation by 50% was reported to the chemist requesting the screen. If the $IC_{50}$ value was less than 0.625 µg/ml, additional serial dilutions were made and tested for activity.

MTT Assay for Cell Number. MTT or 3-(4,5-Dimethylthiazol-2-yl)-2,5-diphenyl-tetrazolium bromide is used in an established method (J. Immunol. Methods, 1983, 65: 55–63) to enumerate cells rather than "Coulter counting". For screening purposes, the correlation between percent inhibition determined for actual crude extracts with the Coulter counter and MTT method was very good (r=o.953, n=102 separate determinations of activity at 20 µg/ml), and no extract that was positive as determined by actual cell counts was lost using the MTT assay. Additional results indicated that the MTT assay yielded very similar values for $IC_{50}$'s in parallel determinations with Coulter counting.

HUMAN TUMOR CELL LINE ASSAY

Maintenance of Cell Line

HCT-8 human colon tumor cells are grown in RPM1 1640 medium (GIBCO). A549 human lung carcinoma cells and T47D human breast carcinoma cells are cultured in Dulbecco medium (Biologos, Inc.). All media are supplemented with 10% fetal bovine serum and contain 50 µg/ml gentamicin. All human tumor cell lines are incubated in 5% $CO_2$ at 37° C. and subcultured once a week.

Procedure

1. Seed 1 ml of cells (5000 HCT-8, 8000 A549, 12000 T47D) into each well of a 24-well plate.
2. Incubate in a $CO_2$-incubator for 48 hours.
3. Add compound to each well and incubate for an additional 120 hours.
4. Discard medium and stain with methylene blue (HCT-8) or crystal violet (A549 & T47D).

5. Compare density of drug-treated well with that of the control (no drug added) as follows: ND (not detectable) >90%, 1+ =75–90%, 2+ =50–74%, 3+ =25–49%, 4+ = <25% of control growth.

Final conc. of Vinblastine or Vincristine control (use 2 μl/assay).

| Solution conc | Amt. added | Final conc. in test |
|---|---|---|
| 50 mg/ml | 2 μl | 50 μg/ml |
| 20 mg/ml | 2 μl | 20 μg/ml |
| 5.0 mg/ml | 2 μl | 5.0 μg/ml |
| 0.5 mg/ml | 2 μl | 0.5 μg/ml |

For solvents other than water, allow solvent to evaporate from tube or well in hood. Always run a solvent control in duplicate in the last two wells of each plate or four tubes for each rack of 72 or fewer tubes. Also run four wells or tubes with media and cells only per run of plates or tubes. When using volumes of aqueous solutions greater than 200 ml, dry sample and bring to desired concentration in media.

Results of the in vitro antitumor assay of compounds 1–9 are summarized in Table 1.

TABLE 1

| ASSAY | COMPOUNDS | | | | | | | | |
|---|---|---|---|---|---|---|---|---|---|
|  | 1 | 2 | 3 | 4 | 5 | 6 | 7 | 8 | 9 |
| P388 IC$_{50}$: (ug/ml) | 2.0 | 7.0 | 4.0 | 4.0 | 0.3 | 12.0 | 2.5 | 1.8 | >20 |
| HCT-8: |  |  |  |  |  |  |  |  |  |
| 50 pg/ml | 4+ | 4+ |  |  |  |  |  |  |  |
| 20 pg/ml | 4+ | 4+ | NT | NT | NT | NT | NT | NT | NT |
| 5 pg/ml | 1+ | ND$^b$ |  |  |  |  |  |  |  |
| 0.5 pg/ml | ND | ND |  |  |  |  |  |  |  |
| A549: |  |  |  |  |  |  |  |  |  |
| 50 pg/ml | 4+ | 4+ |  |  |  |  |  |  |  |
| 20 pg/ml | 4+ | 4+ | NT | NT | NT | NT | NT | NT | NT |
| 5 pg/ml | ND | ND |  |  |  |  |  |  |  |
| 0.5 pg/ml | ND | ND |  |  |  |  |  |  |  |
| T47D: |  |  |  |  |  |  |  |  |  |
| 50 pg/ml | 4+ | 4+ |  |  |  |  |  |  |  |
| 20 pg/ml | 4+ | 3+ | NT | NT | NT | NT | NT | NT | NT |
| 5 pg/ml | 2+ | 2+ |  |  |  |  |  |  |  |
| 0.5 pg/ml | ND | ND |  |  |  |  |  |  |  |

$^a$NT = not tested
$^b$ND = not detected

Table 1 shows that topsentin class compounds 1–8 have good antitumor activity at concentrations of 20 μg/ml or less.

Procedure for P388 In-Vivo Assays

P388 leukemia obtained from DBA/2 mice was inoculated ip into BDF1 mice. The inoculum level was $10^6$ cells in 0.1 ml. Mice were randomized on day 1 into groups of six mice since bacteriological check of tumor was negative. Test materials were dissolved or suspended in sterile 0.98% NaCl solution with the aid of absolute ethanol and "Tween-80", then administered ip, qD1-5, in a volume of 0.5 ml/mouse. Mice were weighed on days 1 & 5 to provide evidence of toxicity and deaths were recorded daily. Each test included appropriate numbers of untested control mice, one-dose level of the positive reference compound 5-fluorouracil and test material (four dose levels each). Test material were prepared fresh on day 1 and administered daily for five days. Quantity and consistency of test material precluded fresh preparation daily. Doses were derived from prior single treatment acute toxicity assays. The endpoints for therapeutic evaluation were mean and median survival time and long-term survivors on day 30. A 25% percent increase in life span (%ILS) was considered evidence of significant activity.

Table 2 reports the in vivo antitumor assay results for compounds 1 & 2.

TABLE 2

| Dose mg/kg | Treatment (days) | Survival % T/C |
|---|---|---|
| | Compound 1 | |
| 300 | 1- 5 | 110 |
| 150 | 1-5 | 132 |
| 75 | 1-5 | 116 |
| 37.5 | 1-5 | 111 |
| | Compound 2 | |
| 300 | 1-4 | toxic |
| 150 | 1-5 | 116 |
| 75 | 1-5 | 111 |
| 37.5 | 1-5 | 105 |

It is apparent from the in vitro and in vivo testing and results reported in Tables 1 & 2 that the compounds of the invention are effective for inhibiting or destroying certain tumors and therefore in controlling diseases caused by or related to such tumors, e.g., cancerous cachexia.

Antiviral Activities of Compounds of the Invention

The following assay methods were utilized to evaluate the in vitro activity of compounds of the invention.

ANTIVIRAL DISC ASSAY FOR HSV-1

A. Maintenance of Cell Cultures

1. Virus a. Herpes simplex type 1 (HSV-1) replicates in the CV-1 cell line. CV-1 is a fibroblast-like cell culture derived from primary African green monkey cells.

2. Growth of CV-1 Cells a. Seed 150 cm$^2$ tissue culture flasks each with $10 \times 10^6$ CV-1 cells in 40 ml of EMEM with 10% FBS (growth medium).

b. Seven days after seeding the flasks, cell numbers should be approximately $40$–$50 \times 10^6$. CV-1 cells have a doubling time of 72 hours based on these numbers.

3. Trypsinization a. Aseptically remove the medium b. Rinse cell sheet two times with 10 ml of Ca$^{++}$- and Mg$^{++}$-free Dulbecco's phosphate buffered saline.

c. Add 1.5 to 2.0 ml of trypsin-EDTA mixture.

d. Incubate flask at room temperature for 10 minutes.
e. Shake flask.
f. Add 10 ml EMEM growth medium and break up cell clumps with pipetting.
g. Count cells.

B. Preparation of plates for viral assays

Cell Concentration a. Dilute the cells with EMEM to $4 \times 10^5$ cells/ml.
b. See 24-well trays with 0.5 ml per well. Cell concentration is $2 \times 10$ cells.
c. Incubate at 37 C. for 1.5 hours.
d. The wells can be used over the next several days beginning the day after seeding (preferably 2, 3, or 4).

C. Assay of HSV-1 in CV-cells

Infection of CV-1 cells in plates with virus
a. Remove medium from wells.
b. Infect well with at least 25 and no more than 80 plaque forming units (PFU) of virus.
c. Incubate infected cells at 37 C. for 1.5 hrs.
d. Pour off supernatant at end of incubation period.
e. Add 0.5 ml of methylcellulose overlay medium (MCO). MCO is a maintenance medium without phenol red made with 1% 4000 centipose methylcellulose. FBS is used at 5% level.

Drug Evaluation a. For drug evaluation wet filter paper discs (6 mm dia.) with approx. 0.02 ml of test compound. Allow solvent to evaporate for 20-30 mins. at ambient temperature, then place discs in the well containing CV-1 cells, virus and MCO.
b. Incubate tissue culture plates for 48 hrs. at 37 C.
c. After 48 hrs. place 0.5 ml NRMCO on each well. (NRMCO is a maintenance overlay medium without phenol red containing 0.1 mg neutral red dye/ml and 2% 15 Cps. methylcellulose.
d. Incubate plates at 37 C. and read the following day. Antiviral activity should be observed from two parameters. One is actual reduction in the number of plaques and two is the diminution in plaque diameter.

Scoring Drug Activity a. Antiviral activity (AVA) is scored from 0 to +++.
+++ =complete inhibiton of plaque formation
++ =partial inhibition
+ =partial inhibition
0=no protection
b. Cytotoxicity (Cyt)
0=no visual or microscopic cytotoxicity
16=complete cell destruction
8, 10, 12, 14=partial cytotoxicity.

Antiviral Assay for Mouse Coronavirus Strain A59

When NCTC 1469 cells (a clone of mouse liver cells) are infected with mouse coronavirus A59, the cytopathic effects (CPE) which result are characterized by giant cell formation, cell fusion, and cell destruction. Cell fusion observed in NCTC 1469 cell cultures infected with strain A59 can be observed microscopically in 12 hours and when stained with methylene blue dye the syncytia are visible to the eye as dark blue foci on the fixed cell sheet. Twenty-four hours after infection cell fusion and cytopathic effects are extensive and the assays can be read both macroscopically and microscopically. Compounds with antiviral activity can be identified by comparing the CPE in drug treated cultures to that observed in untreated infected cells.

Assay Protocol

1. Cells
NCTC clone 1469, a derivative of mouse liver, ATCC No. CCL 9.
2. Virus
Mouse hepatitis virus strain MHV-A59 classified as a corona virus, ATCC No. 764
3. Media
Growth medium
NCTC 135
10% horse serum,
2% 1-glutamine (200 mM)
1% nonessential amino acids (NEAA) (100×)
1% sodium pyruvate (110 mg/liter) (100×)
50 µg/ml gentamicin Maintenance medium Dulbecco's modified Eagle's minimum essential medium in Earle's balanced salt solution (4500 mg/liter glucose) (D-EMEM)
5% fetal bovine serum
2% 1-glutamine (200 mM)
1% nonessential amino acid (NEAA) (100×)
1% sodium pyruvate (110 mg/liter) (100×)
50 µg/ml gentamicin Trypsin solution 0.5 mg/ml trypsin, 0.2 mg/ml EDTA.4Na, and 1.1 mg/ml glucose in Dulbecco's phosphate buffered saline without $CaCl_2$ and $MgCl.6H_2O$ (PBS)

Methylene blue stain 5 grams methylene blue/liter
50% ethanol:water
4. Growth of NCTC 1469 cell line
Confluent cultures are exposed briefly to the trypsin solution and flasks are shaken hard to remove cells from the plastic. For a 150 ml flask add 4 ml of trypsin solution and reduce volume for smaller cell areas. Subcultures for cell maintenance are seeded at $10 \times 10^6$ cells in 40 ml growth medium for 150 ml tissue culture flask. Cells are subcultured twice a week.
5. Antiviral assay
Plates (24 well, 16 mm diameter/well) are seeded with between $7.5 \times 10^5$ and $1 \times 10^6$ cells in 1 ml growth medium per well. Plates are incubated 24 hours at 37 C. in 5% $CO_2$. The growth medium is removed and the cultures are infected with 0.2 ml A59 diluted in PBS with calcium and magnesium to contain approximately 100 infectious doses of virus. Plates are incubated at 37 C. for 1 hour in 5% $CO_2$. Viral supernatants are removed and replaced with maintenance medium only or medium containing drug solutions. The drug solutions are prepared by adding diluted samples to glass tubes and allowing solvents to evaporate. Ten lambda of dimethyl sulfoxide is added to each tube to solubilize drug material and 1 ml maintenance medium is added to the tube. The fluid from each tube is transferred to the NCTC 1469 cells infected with A59 virus.

Cytopathic effects can be observed in 12 hours. Plates are routinely read at 24 hours after fixation and staining with methylene blue dye.

Drug cytotoxicity

Cell viability is used to determine drug cytotoxicity.
100% = complete cell destruction
75% = partial cell destruction
50% = partial cell destruction
25% = partial cell destruction
0% = no cytotoxicity

Antiviral activity

+++ = absence of CPE and cell fusion
++ = partial inhibition
+ = partial inhibition
± = marginal inhibition
0 = no protection The fifty percent minimum inhibitory concentration ($MIC_{50}$) is determined by estimating the percent reduction in CPE compared to the controls from the inhibition values with +++ = 100% reduction, ++ = 75%, + = 50%, ± = 25%, and — = no reduction in plaque number compared to controls.

The results of the HSV-1 antiviral activity assays on compounds 1, 2, 5, 7, 8 & 9 are reported in Table 3.

TABLE 3

| COMPOUND | DOSE (ug/disk) | CYT. | AVA |
| --- | --- | --- | --- |
| 1 | 200 | 0 | ++ |
|   | 50 | 0 | + |
|   | 20 | 0 | — |
| 2 | 200 | 0 | ++ |
|   | 50 | 0 | — |
| 5 | 20 | 0 | — |
| 7 | 20 | 0 | — |
| 8 | 20 | 0 | — |
| 9 | 20 | 0 | — |

The results of the HSV-1 antiviral activity assays on compounds 1-9 are reported in Table 4.

TABLE 4

| COMPOUND | DOSE (µg/disk) | CYT. | AVA |
| --- | --- | --- | --- |
| 1 | 20 | 0 | +++ |
|   | 2 | 0 | +++ |
|   | 0.2 | 0 | — |
| 2 | 10 | 0 | ++ |
|   | 5 | 0 | — |
| 3 | 20 | 0 | +++ |
|   | 2 | 0 | — |
| 4 | 20 | 0 | +++ |
|   | 2 | 0 | — |
| 5 | 20 | 0 | ++ |
|   | 2 | 0 | — |
| 6 | 20 | 0 | +++ |
|   | 2 | 0 | ++ |
| 7 | 20 | 0 | — |
| 8 | 20 | 0 | — |
| 9 | 20 | 0 | — |

It is apparent from the in vitro testing that the compounds of the invention are effective for inhibiting viral growth and for controlling virus related diseases such as Herpes and the common cold.

Therapeutic application of the new compounds and compositions containing them can be contemplated to be accomplished by any suitable therapeutic method and technique presently or prospectively known to those skilled in the art. Further, the compounds of the invention have use as starting materials or intermediates for the preparation of other useful compounds and compositions.

In accordance with the invention, pharmaceutical compositions comprising, as active ingredient, an effective amount of one or more of the new compounds and one or more non-toxic, pharmaceutically acceptable carriers or diluents. Examples of such carriers for use in the invention include ethanol, dimethyl sulfoxide, glycerol, silica, alumina, starch and equivalent carrier and diluents. While effective amounts may vary, as conditions in which such compositions are used vary, a minimal dosage required for antitumor activity is generally between 0.01 and 100 micrograms of the new compound against $10^5$ tumor cells and a minimal dosage required for antiviral activity is generally between 50 and 200 micrograms against 25-80 plaque-forming units of virus. To provide for the administration of such dosages for the desired therapeutic treatment, new pharmaceutical compositions of the invention will advantageously comprise between about 0.1% and 45%, and especially, 1 and 15%, by weight of the total of one or more of the new compounds based on the weight of the total composition including carrier or diluent.

The embodiments of the invention in which an exclusive property of privilege is claimed are defined as follows:

1. A substantially pure compound of the formula:

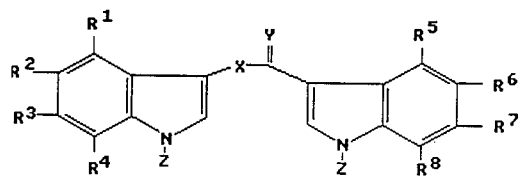

Wherein X =

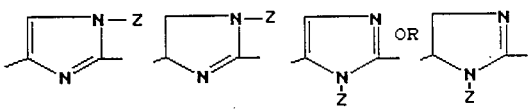

$R^{1-8}$ are the same or different selected from —H, —OH, halogen, —R, —OR, —OCOR, or —OA;

Y is the single group O, or two groups, same or different, selected from —H, —OH, —OR, or —OCOR;

Z are the same or different selected from —H, —R;

R is C1-5 alkyl and A is —R-phenyl.

2. A substantially pure compound of the formula:

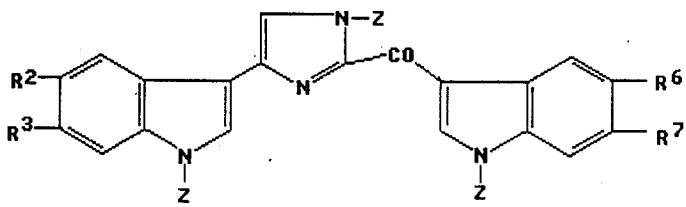

wherein R² & R⁶ are —H while R³ & R⁷ are —H, —OH, halogen, —R, —OR, —OCOR or —OA; or R³ & R⁷ are —H while R² & R⁶ are —H, —OH, halogen, —R, —OR, —OCOR or —OA; Z are the same or different selected from —H, —R; R is C1-5 alkyl and A is —R-phenyl.

3. A substantially pure compound of the formula:

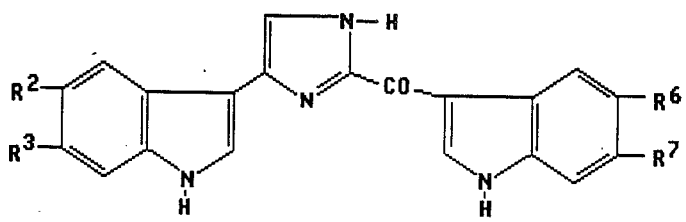

wherein:
1: $R^2$, $R^3$, $R^6$=H; $R^7$=OH
2: $R^2$, $R^6$=H; $R^3$=Br; $R^7$=OH
4: $R^2$, $R^6$, $R^7$=H; $R^3$=OH,
5: $R^2$, $R^6$=H; $R^3$, $R^7$=OH,
6: $R^2$, $R^3$, $R^6$, $R^7$=H
7: $R^2$, $R^3$, $R^7$=H; $R^6$=OH
8: $R^3$, $R^6$, $R^7$=H; $R^2$=OH,
9: $R^2$, $R^6$=OH; $R^3$, $R^7$=H.

4. A compound of claim 1 according to the formula:

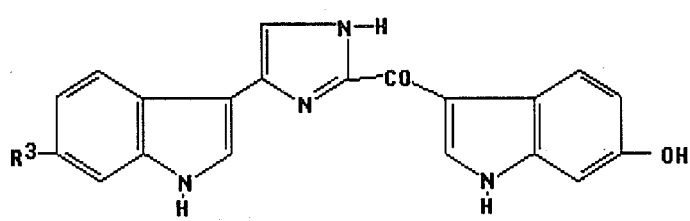

wherein $R^3$ is hydrogen or bromine.

5. A pharmaceutical composition comprising between about 0.1% and 45% by weight, based on the total weight of said composition, as an active ingredient one or more of the compounds of claim 1 and a nontoxic pharmaceutically acceptable carrier or diluent.

6. A pharmaceutical composition comprising between about 0.1% and 45% by weight, based on the total weight of said composition, as an active ingredient one or more of the compounds of claim 2 and a nontoxic pharmaceutically acceptable carrier or diluent.

7. A pharmaceutical composition comprising between about 0.1% and 45% by weight, based on the total weight of said composition, as an active ingredient one or more of the compounds of claim 3 and a nontoxic pharmaceutically acceptable carrier or diluent.

8. A pharmaceutical composition comprising between about 0.1% and 45% by weight, based on the total weight of said composition, as an active ingredient one or more of the compounds of claim 4 and a nontoxic pharmaceutically acceptable carrier or diluent.

* * * * *